(12) United States Patent
Park et al.

(10) Patent No.: US 9,446,129 B2
(45) Date of Patent: Sep. 20, 2016

(54) MULTI-LAYERED STRUCTURE FOR DRUG RESERVOIR AND DRUG ELUTING STENT INCLUDING THE SAME

(71) Applicant: AJOU UNIVERSITY INDUSTRY-ACADEMIC COOPERATION FOUNDATION, Suwon, Gyeonggi-do (KR)

(72) Inventors: Ki Dong Park, Seoul (KR); Jong Hoon Choi, Gyeonggi-do (KR)

(73) Assignee: AJOU UNIVERSITY INDUSTRY-ACADEMIC COOPERATION FOUNDATION, Suwon, Gyeonggi-Do (KR)

( * ) Notice: Subject to any disclaimer, the term of this patent is extended or adjusted under 35 U.S.C. 154(b) by 0 days.

(21) Appl. No.: 14/309,911

(22) Filed: Jun. 20, 2014

(65) Prior Publication Data

US 2014/0377322 A1    Dec. 25, 2014

(30) Foreign Application Priority Data

Jun. 20, 2013    (KR) ........................ 10-2013-0071248

(51) Int. Cl.
| | | |
|---|---|---|
| A61K 9/70 | (2006.01) | |
| A61K 45/06 | (2006.01) | |
| A61K 31/137 | (2006.01) | |
| A61K 31/337 | (2006.01) | |
| A61K 31/727 | (2006.01) | |
| A61L 33/00 | (2006.01) | |
| A61L 27/52 | (2006.01) | |
| A61L 31/10 | (2006.01) | |
| A61L 31/16 | (2006.01) | |
| A61K 47/48 | (2006.01) | |

(52) U.S. Cl.
CPC ............. *A61K 45/06* (2013.01); *A61K 31/137* (2013.01); *A61K 31/337* (2013.01); *A61K 31/727* (2013.01); *A61K 47/48215* (2013.01); *A61L 27/52* (2013.01); *A61L 31/10* (2013.01); *A61L 31/16* (2013.01); *A61L 33/0011* (2013.01); *A61L 2420/08* (2013.01)

(58) Field of Classification Search
None
See application file for complete search history.

(56) References Cited

U.S. PATENT DOCUMENTS

2009/0076606 A1* 3/2009 Huerta ................ A61F 2/30767
                                                                623/16.11
2011/0052788 A1* 3/2011 Messersmith ........ C08G 65/332
                                                                427/2.1

FOREIGN PATENT DOCUMENTS

| KR | 10-2004-0028486 A | 4/2004 | |
| WO | WO 2011/028031 | * 3/2011 | ............. A61L 27/32 |

OTHER PUBLICATIONS

Torchilin, Targeted polymeric micelles for delivery of poorly water soluble drug, CMLS Cell Mol. Life Sci. 2004, vol. 61, p. 2551.*

* cited by examiner

*Primary Examiner* — Bethany Barham
*Assistant Examiner* — Ping Cao
(74) *Attorney, Agent, or Firm* — Revolution IP, PLLC

(57) ABSTRACT

Disclosed is a multi-layered structure for drug reservoir, comprising a first micelle layer for crosslinking and adhesion, comprising a drug, a multi-arm polymer, a phenol derivative, and a dopa derivative and having a one or two-layered structure; a second micelle layer for crosslinking, being stacked on the first micelle layer, comprising a drug, a multi-arm polymer, and a phenol derivative, and having a one or two-layered structure; and a physiologically active material layer, being stacked on the second micelle layer, comprising a physiologically active material, a water-soluble polymer, and a phenol derivative, and having a one or two-layered structure.

3 Claims, 4 Drawing Sheets

MULTI-LAYERED STRUCTURE FOR DRUG RESERVOIR AND DRUG ELUTING STENT INCLUDING THE SAME

RELATED APPLICATION

This application claims the benefit of Korean Patent Application No. 10-2013-0071248, filed on Jun. 20, 2013, in the Korean Intellectual Property Office, the disclosure of which is incorporated herein in its entirety by reference.

BACKGROUND

1. Field

One or more embodiments of the present invention relate to a multi-layered structure for drug reservoir and a drug-eluting stent including the same.

2. Description of the Related Art

Recently, as the population ages, demands of implantable therapeutic devices, such as a vascular stent for coronary artery and peripheral artery, have been increased, and accordingly, imports of these devices are steadily increasing.

However, after surgery, implanted vascular stents may cause, thrombosis-induced acute obliterating, and stents themselves may act as a traumatic factor with respect to endovascular membrane, thereby causing intimal hyperplasia and then restenosis.

Accordingly, together with a surface treatment to suppress thrombosis, functional surface reformation techniques for embodying a drug-eluting function that allows a therapeutic drug to be directly delivered into blood vessels are required.

In response, Hepacoat Company et al. commercialized a stent that is coated with heparin suppressing thrombosis, and Cordis Company produced, as a drug-eluting stent for the suppression of vascular restenosis, Cypher™. However, these stents caused, for example, death of patients who recently received stent implantations. Accordingly, there is a need to develop stents that have improved drug-eluting performance.

Korean Patent Publication No. 2004-0028486 discloses a drug-release antithrombogenic multi-layer coated stent and a method of preparing the same, wherein the stent enables biologically active agents to be carried to provide localized treatment at the implant site. However, a drug-eluting stent including a micelle layer stacked using a phenol derivative, such as tyramine, has not been disclosed.

SUMMARY

Provided is a drug-eluting stent that suppresses stent restenosis and thrombosis, which are problems of a conventional drug-eluting stent, and that enables controllable elution of a drug.

Additional aspects will be set forth in part in the description which follows and, in part, will be apparent from the description, or may be learned by practice of the presented embodiments.

According to an aspect of the present invention, a multi-layer structure for drug reservoir includes a first micelle layer for crosslinking and adhesion including a drug, a multi-arm polymer, a phenol derivative, and a dopa derivative, and having a one or two-layered structure; a second micelle layer for crosslinking, being stacked on the first micelle layer, including a drug, a multi-arm polymer, and a phenol derivative, and having a one or two-layered structure; and a physiologically active material layer, being stacked on the second micelle layer, including a physiologically active material, a water-soluble polymer, and a phenol derivative, and having a one or two-layered structure.

The multi-arm polymer may include at least one polymer selected from the group consisting of at least one multi-arm polyethyleneglycol selected from the group consisting of (3-arm)-polyethyleneglycol (3armPEG), (4-arm)-polyethyleneglycol(4armPEG), (6-arm)-polyethyleneglycol (6armPEG), and (8-arm)-polyethyleneglycol (8armPEG); and Tetronic® series (4arm-PPO-PEO).

The phenol derivative may include at least one selected from the group consisting of tyramine, a hydroxyphenylacetic acid, and a hydroxypropionic acid.

The dopa derivative may include at least one selected from the group consisting of L-dihydroxyphenylalanine (L-DOPA), dopamine, norepinephrine, epinephrine, and dopaquinone.

The water-soluble polymer may include at least one selected from the group consisting of polyethyleneglycol (PEG), polyethyleneoxide (PEO), polyethyleneimine (PEI), polyvinylalcohol (PVA), and a copolymer of these. The copolymer may include at least one selected from the group consisting of PEO-PPO-PEO (Pluronic® series), PEO-PPO-PEO (Tetronic® series), PEG-PEI, PEG-PVA, PEG-PEI-PVA, and PEI-PVA.

The physiologically active material may include at least one selected from the group consisting of heparin, hyaluronic acid, chitosan, chondroitin sulfate, dextran, fibroblast growth factor (FGF), vascular endothelial growth factor (VEGF), transforming growth factor (TGF), bone morphogenetic protein (BMP), human growth hormone (hGH), porcine growth hormone (pGH), leukocyte growth factor (G-CSF), erythrocyte growth factor (EPO), macrophage growth factor (M-CSF), tumor necrosis factor (TNF), epithelial growth factor (EGF) platelet-derived growth factor (PDGF), interferon-α, β, γ, interleukin-2 (IL-2), calcitonin, nerve growth factor (NGF), growth hormone releasing factors, angiotensin, luteinizing hormone releasing hormone (LHRH), LHRH agonist, insulin, thyrotropin releasing hormone (TRH), angiostatin, endostatin, somatostatin, glucagon, endorphin, bacitracin, mergain, colistin, monoclonal antibody, and vaccines.

The drug may include at least one selected from the group consisting of an antibacterial agent, an anticancer agent, and an anti-inflammatory agent.

The antibacterial agent may include at least one selected from the group consisting of minocycline, tetracycline, ofloxacin, phosphomycin, mergain, profloxacin, ampicillin, penicilin, doxycycline, thienamycin, cephalosporin, norcadicin, gentamycin, neomycin, kanamycin, paromomycin, micronomycin, amikacin, tobramycin, dibekacin, cefotaxime, cephaclor, erythromycin, ciprofloxacin, levofloxacin, enoxacin, vancomycin, imiphenem, and fucidic acid.

The anticancer agent may include at least one selected from the group consisting of paclitaxel, taxotare, adriamycin, endostatin, angiostatin, mitomycin, bleomycin, cisplatin, carboplatin, doxorubicin, daunorubicin, idarubicin, 5-fluorouracil, methotrexate, and actinomycin.

The anti-inflammatory agent may include at least one selected from the group consisting of acetaminophen, aspirin, ibuprofen, diclofenac, indomethacin, piroxicam, fenoprofen, flubiprofen, ketoprofen, naproxen, suprofen, loxoprofen, cinoxicam, and tenoxicam.

According to an aspect of the present invention, a drug-eluting stent includes a stent and the multi-layered structure stacked on the stent.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
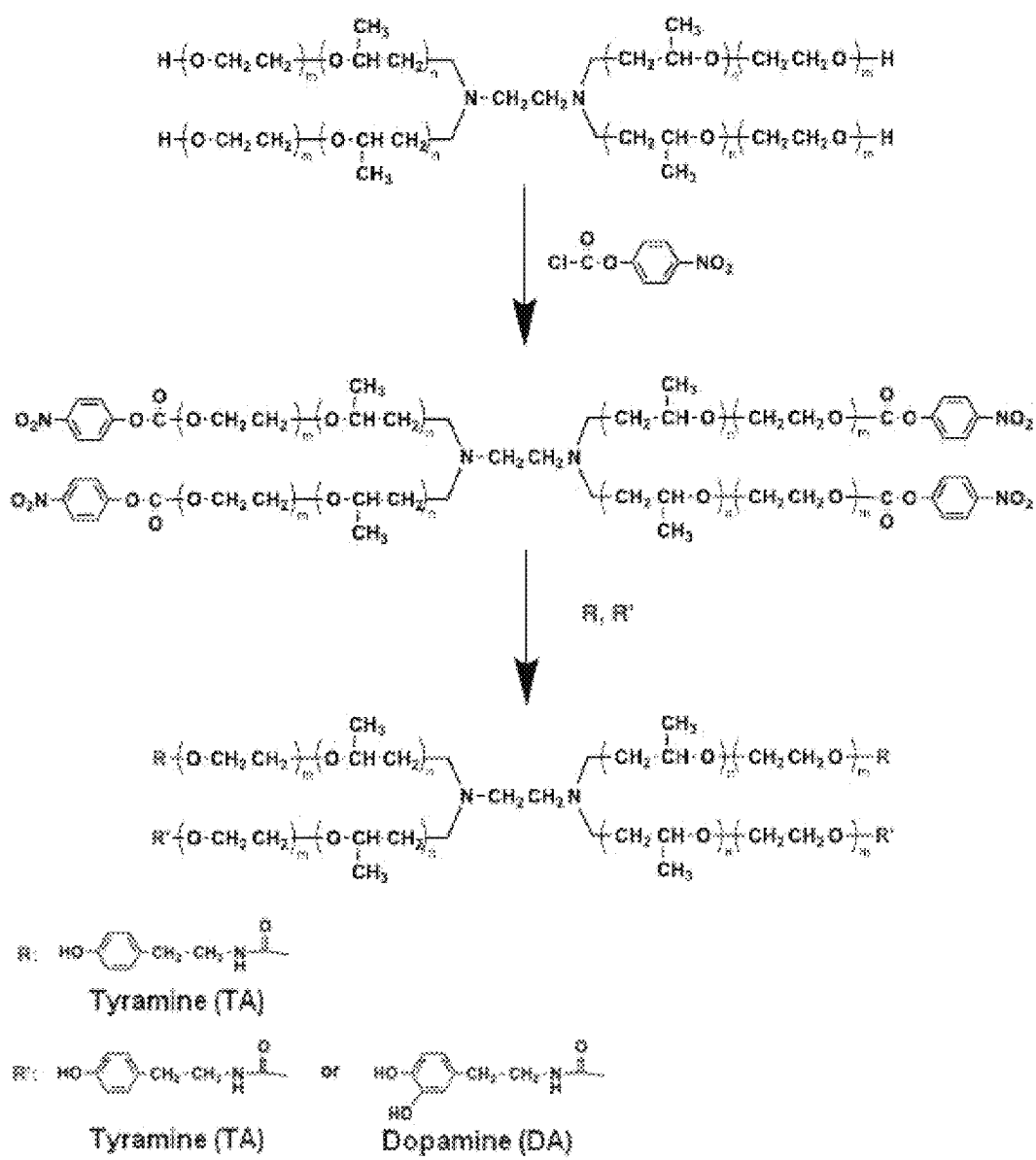
FIG. 1 illustrates a method of preparing a Tetronic®-tyramine/dopamin conjugate or a Tetronic®-tyramine conjugate
Figure 2:
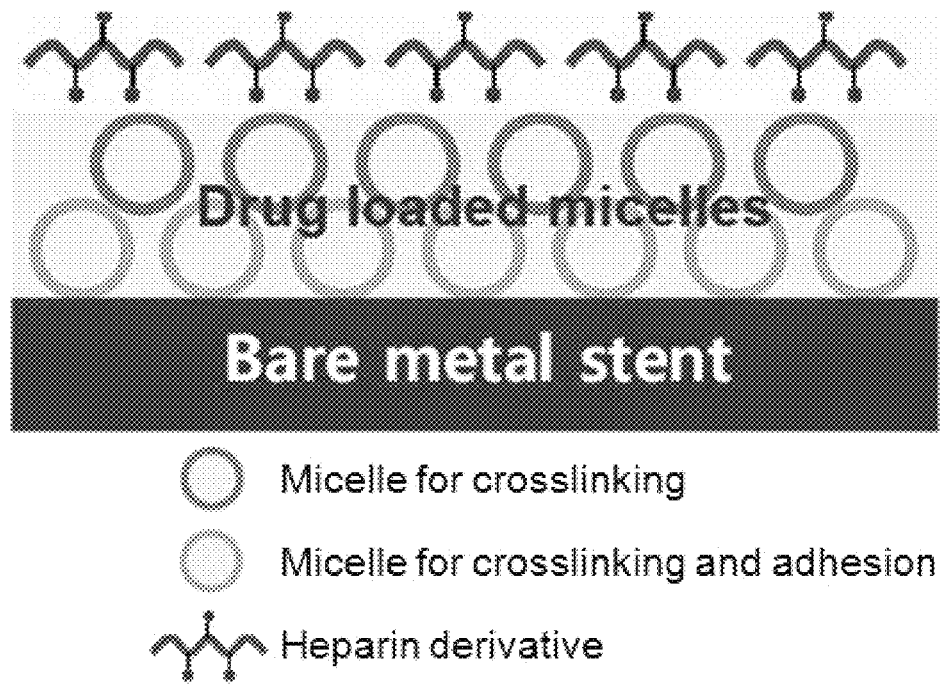
FIG. 2 shows a schematic view of a drug-eluting stent according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, to explain the present invention in detail, a multi-layered structure for drug reservoir and a drug-eluting stent including the same according to embodiments will be described. The multi-layered structure includes paclitaxel that is a drug, a tetronic polymer that is a multi-arm polymer, tyramine that is a phenol derivative, dopamin that is a dopa derivative, heparin that is a physiologically active material and polyethyleneglycol that is a water-soluble polymer.

First, a tetronic-tyramine(TA)/dopamin(DA) conjugate used in a first micelle layer may be prepared according to the method illustrated in FIG. 1. In detail, tetronic-p-nitrophenylchloroformate (PNC) is synthesized, and then, tyramine and dopamine are added thereto to produce a tetronic-tyramine(TA)/dopamin(DA) conjugate.

A tetronic-tyramine (TA) conjugate used in a second micelle layer may also be prepared according to the method illustrated in FIG. 1. In detail, tetronic-p-nitrophenylchloroformate (PNC) is synthesized, and then, tyramine is added to prepare tetronic-tyramine(TA) conjugate.

The tetronic-tyramine(TA)/dopamin(DA) conjugate and the tetronic-tyramine(TA) conjugate may each be dissolved in water, and then, a paclitaxel (PTX) solution is added to each solution to prepare a paclitaxel(PTX)-containing first micelle layer and a paclitaxel(PTX)-containing second micelle layer.

Regarding a physiologically active material layer, first, PNC-PEG-PNC is synthesized, and then, tyramine(TA) and an amine compound are added to a PNC-PEG-PNC solution to synthesize $NH_2$-PEG-TA, and heparin is added to a $NH_2$-PEG-TA solution to prepare heparin-PEG-TA.

A drug-eluting stent according to an embodiment of the present invention may be prepared as follows. The first micelle layer is stacked at least once, for example, one to three times, on a metal stent. The first micelle layer is formed on the metal stent due to crosslinking of tyramin and adhesion of dopamin. Thereafter, the second micelle layer is stacked at least once, for example, 10 to 30 times, on the first micelle layer. The second micelle layer may be formed on the first micelle layer due to crosslinking of tyramine. Then, the physiologically active material layer is stacked at least once, for example one to three times, on the second micelle layer. The physiologically active material, such as heparin, may cause antithrombogenic effects.

Hereinafter, examples of the present invention will be described to help understanding of the present invention. However, these examples are provided herein for illustrative purpose only, and do not limit the scope of the present invention. Examples of the present invention are provided to fully explain the present invention to those skilled in the art.

EXAMPLE 1

Formation of Tetronic®-TA/DA Conjugate

Tetronic®-TA/DA formed via urethane bond was prepared according to the reaction scheme as shown in FIG. 1. Hydroxyl groups at terminals of Tetronic® were activated using excess p-nitrophenylchloroformate (PNC). Then, tyramine (TA) and dopamine (DA) were added thereto, and the resultant mixture was stirred to produce a Tetronic®-TA/DA conjugate.

1. Synthesis of Tetronic®-PNC

Tetronic® (30 g) was dissolved in 300 ml of dioxane. Tetronic® used herein was Tetronic® 1307, and was a block copolymer having 4-arm-(polypropylene oxide)-(polyethylene oxide). The solution of Tetronic® dissolved in dioxane was stirred at room temperature in nitrogen atmosphere for 20 minutes, and then, a solution prepared by dissolving 1.018 g of 4-dimethylaminopyridine (DMAP) and 0.843 g of triethylamine (TEA) in 40 ml of dioxane and a solution prepared by dissolving 1.679 g of PNC in 50 ml of dioxane were sequentially added thereto. Thereafter, the result was stirred at a temperature of 30° C. for 24 hours while the nitrogen atmosphere was maintained. Thereafter, the mixture was filtered under reduced pressure to remove precipitated side-reaction materials, and then, the mixture was concentrated to a high concentration by using a rotator evaporator. The condensed mixture was slowly added to cold diethylether to cause precipitation, and then, the result was filtered under reduced pressure to obtain precipitates, which were then dried under reduced pressure to obtain Tetronic®-PNC in the form of white powder.

2. Synthesis of Tetronic-TA/DA

The synthesized tetronic-PNC was dissolved in 100 ml of dimethylsulfoxide (DMSO), and in the nitrogen atmosphere, the resultant solution was stirred for 15 minutes, and then, a solution of TA dissolved in 50 ml of DMSO and a solution of DA dissolved in 50 ml were added thereto, and the mixture was stirred for 24 hours to obtain a tetronic-TA/DA conjugate. Thereafter, the conjugate was allowed to penetrate with respect to ammonium oxide to remove a PNC salt, and then subjected to dialysis for 3 days by using methanol and ethanol to remove non-reacted tyramine and dopamine and other reaction side-products. In this regard, during dialysis, a molecular weight cut-off value used for dialysis was 3500 Da or more. The resultant solution was concentrated and precipitated in diethylether, and then, filtered under reduced pressure, and dried under reduced pressure to obtain a tetronic-TA/DA conjugate in the form of white powder. The structure of tetronic-TA/DA was identified by $^1$H NMR (400 MHz, Varian).

EXAMPLE 2

Formation of Tetronic-TA Conjugate

1. Synthesis of Tetronic-PNC Conjugate
This experiment was performed in the same manner as in Example 1.
2. Synthesis of Tetronic-TA Conjugate
This experiment was performed in the same manner as in 2 of Example 1, except that only tyramine (TA) was used and dopamin (DA) was not used.

EXAMPLE 3

Preparation of Paclitaxel (PTX)-Containing Tetronic-TA/DA(PTTD) and Paclitaxel (PTX)-Containing Tetronic-TA(PTTA) Nanoparticles Tetronic-TA/DA conjugate and tetronic-TA conjugate were each dissolved in distilled water, and then, PTX dissolved in ethanol was added thereto, and then stirred at a temperature of 37° C. for 24 hours. Thereafter, to remove residual PTX, the result was centrifuged (3,500 rpm, 30 minutes), and then, a supernatant was collected. The supernatant was sonicated and lyophilized to obtain nanoparticles.

EXAMPLE 4

Formation of Heparin-PEG-TA (HPT)

1. Synthesis of PNC-PEG-PNC
Polyethyleneglycol (PEG) was dissolved in dioxane. PEG used herein had a molecular weight of 4 kDa. A solution prepared by dissolving 0.61 g of DMAP and 0.51 g of TEA in 100 ml of dioxane and a solution prepared by dissolving 1.01 g of PNC in 20 ml of dioxane were sequentially added to the resultant solution in the nitrogen atmosphere. Thereafter, the result was stirred at a temperature of 30° C. for 24 hours while the nitrogen atmosphere was maintained. Then, the mixture was filtered under reduced pressure to remove precipitated side-reaction materials, and then, concentrated to a high concentration by using a rotator evaporator. The condensed mixture was slowly added to cold diethylether to cause precipitation, and then, filtered under reduced pressure to obtain precipitates, which were then dried under reduced pressure to obtain PNC-PEG-PNC in the form of white powder.
2. Synthesis of NH$_2$-PEG-TA
PNC-PEG-PNC (10 g) prepared in step 1 above was dissolved in dimethylformamide (DMF, 40 ml), and 0.3641 g of tyramine (TA) was dissolved in DMF (40 ml), and then, at a temperature of 30° C. and in the nitrogen atmosphere, a tyramine solution was slowly added dropwise to the PNC-PEG-PNC solution and then stirred for 6 hours.

A solution prepared by dissolving 4.629 g (69.24 mmol) of ethylene diamine in DMF (20 ml) was slowly added dropwise to the resultant mixture and then stirred for 24 hours.

The mixture was filtered under reduced pressure to remove precipitated side-reaction materials, and a filtrate was added dropwise to cold diethylether, and then filtered under reduced pressure, and precipitates were dried under reduced pressure to obtain NH$_2$-PEG-TA in the form of white powder.
3. Synthesis of Heparin-PEG-TA
1 g of heparin was dissolved in 30 ml of 0.1M MES, and then, EDC[1-ethyl-3(3-dimethyl aminopropyl)carbodiimide, 65 mg] dissolved in 1 ml of MES (2-morpholinoethanesulfonic acid) was added thereto. 15 minutes after, NHS (N-hydroxysuccinimide, 19 mg) dissolved in 1 ml of MES was added thereto. 15 minutes after, NH$_2$-PEG-TA (1.42 g) dissolved in 10 ml of 0.1M MES was added thereto, and the result was stirred for 24 hours.

Then, the result was filtered under reduced pressure, and the mixture was filtered through a filtering membrane (a molecular weight cut-off=15,000 Da) for 3 days, and lyophilized to obtain heparin-PEG-TA in the form of white powder.

EXAMPLE 5

Quantification of Paclitaxel Content in PTTA, PTTD Nanoparticles

To break down the structure of nanoparticles, PTTA and PTTD nanoparticles (5 mg) were each dissolved in 1 ml of dichloromethane. Then, the dichloromethane was evaporated, and then, the same volume of a mixture including methanol and acetonitrile (1:1), which acted as a HPLC developing solvent, was added thereto to dissolve PTX. To remove residual dust and non-dissolved materials, a syringe filter (MWCO=0.2 µm) was used for filtering, and then HPLC measurement was performed. As a result, the drug content was identified to be 7.3±0.03%.

EXAMPLE 6

Surface Introduction of PTTD Nanoparticles

A stainless steel (1×1 cm) sample was placed in a 24-well plate, and then, 0.5 ml of PTTD (50 mg/ml) nanoparticles solution suspended in PBS was added thereto, and the result was slowly stirred for an appropriate period of time in an incubator. After time elapsed, the sample was washed with PBS and distilled water and dried, thereby producing a stainless sample coated with PTTD nanoparticles. To measure PTX surface content, the sample coated with PTTD nanoparticles was placed in dichloromethane, and the result was strongly stirred for 1 hour to extract PTX into a dichloromethane layer. Thereafter, the dichloromethane layer was isolated, and dried at a temperature of 40° C. After complete drying, a methanol:acetonitrile (1:1) solution, which was a HPLC developing solvent, was added thereto, and the result was stirred for 30 minutes, and then the result was subjected to filtration through a syringe filter, and then, a PTX content was measured by HPLC. Herein, HPLC analysis was performed using a reversed-phase column, and a flow rate was 0.5 ml/min, and an ultraviolet ray absorption wavelength was set to 229 nm.

Figure 3:
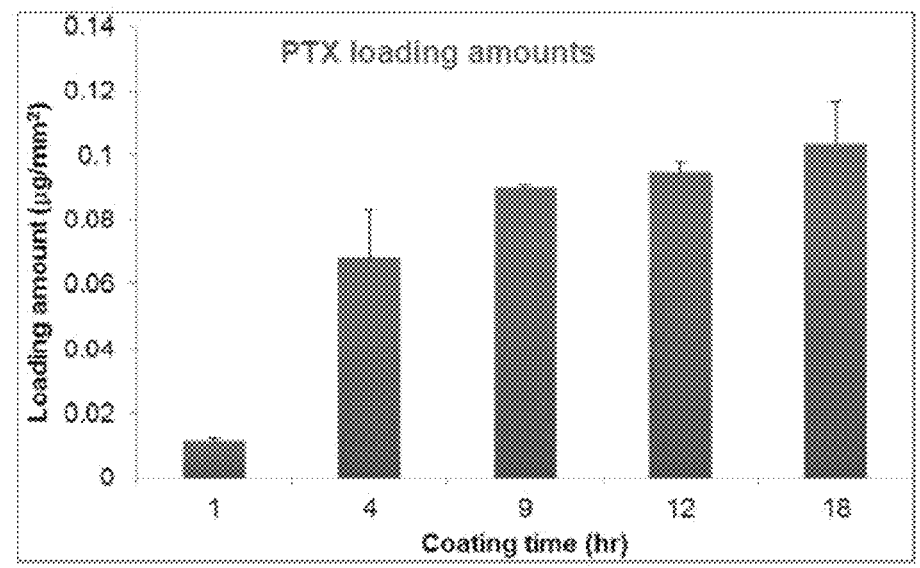
FIG. 3 shows a graph of a loading amount of paclitaxel with respect to a coating time of PTTD nanoparticles.

As a result, as shown in FIG. 3, the longer coating time of PTTD nanoparticles, the greater PTX loading amount.

EXAMPLE 7

Production of Phenol with Surface on which PTTA Nanoparticles are Stacked by Enzymatic Reaction PTTA nanoparticles were dissolved in HRP (horseradish peroxidase, 0.032 mg/ml) solution and H$_2$O$_2$ (0.032 wt %)

solution, respectively. These mixtures (0.25 ml) were poured to a PTTA coated stainless steel substrate.

After incubation for 10 min, the substrate was washed with distilled water. The cycle including adding, incubating, and washing of the same amount of nanoparticles solution was repeated to stack PTTA nanoparticles. PTX contained in the surface was quantified according to the stack count by using the above-stated method.

Figure 4:
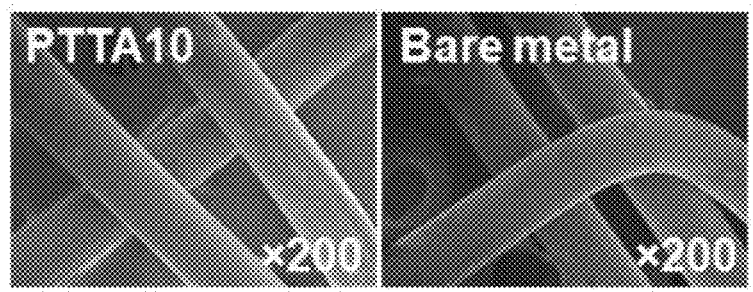
FIG. 4 shows a scanning electron microscope (SEM) of the surface of a sample on which ten layers consisting of PTTA nanoparticles are stacked.
Figure 5:
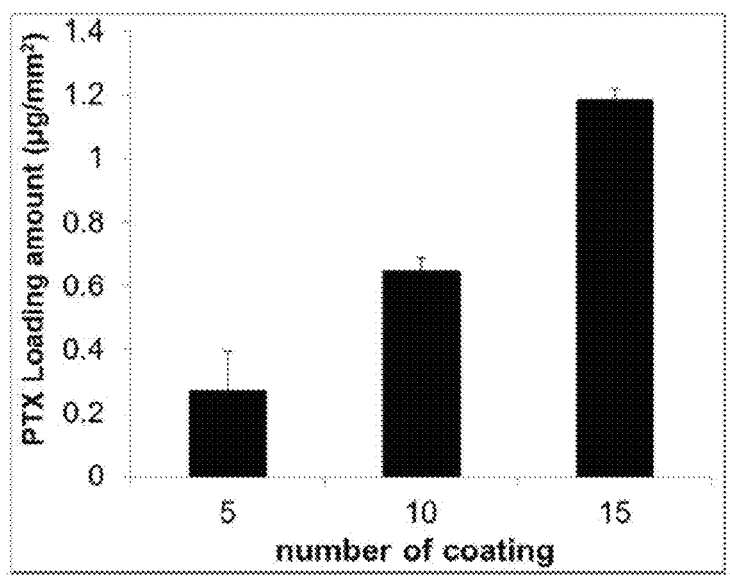
FIG. 5 shows a graph of a loading amount of paclitaxel with respect to coating number of PTTA nanoparticles.

FIG. 4 shows a scanning electron microscope (SEM) image of the surface of the sample on which ten layers consisting of PTTA nanoparticles stacked, and FIG. 5 shows that as the coating number of PTTA nanoparticles increases, the loading amount of PTX increases.

EXAMPLE 8

Production of Phenol with Surface on which HPT are Stacked by Enzymatic Reaction One microliter of HPT (1 mg/ml) dissolved in HRP (0.032 mg/ml) and $H_2O_2$ (0.032 wt %), respectively, was poured to the PTTD or PTTA (10- and 30-layered) introduced substrate as described in Example 7.

Figure 6:
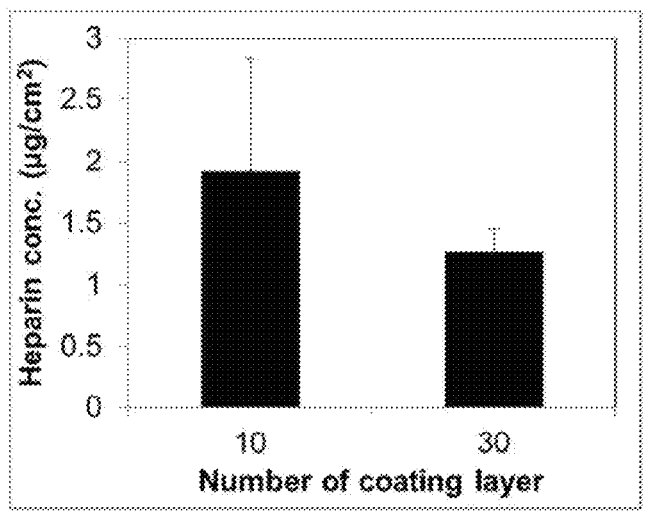
FIG. 6 shows quantitative results of heparin with respect to PTTA coating number of a drug-eluting stent including PTTD, PTTA, and HPT.

After incubation for 10 minutes, the substrates were washed with distilled water. Toluidine Blue analysis was used to quantify heparin stacked on the surface, and the results thereof are shown in FIG. 6.

Also, the anti-coagulation evaluation of stacked heparin was performed using anti-FXa assay according to the guide of the manufacturer, and the results thereof are shown in Table 1.

TABLE 1

| Sample | PTTA 30 + HPT |
| --- | --- |
| Hepain activity (IU/cm$^2$) | 0.16 ± 0.007 |
| Anti-coagulation ability (%) | 85 ± 0.4 |

EXAMPLE 9

Identification of drug-elution behavior on stack structure including PTTD, PTTA and HPT Samples having a surface on which PTTD and PTTA (10-layered, 20-layered, and 30-layered) and HPT were stacked according to Example 8 were placed in a vial, and then, PTX released was collected using PBS (containing 0.05 wt % Tween 20). Thereafter, at appropriate time intervals, a predetermined amount of PBS was replaced with fresh PBS. Dichloromethane was added to the extracted solution to extract PTX, and dichloromethane was evaporated therefrom. Thereafter, the result was dissolved in a mixture of methanol and acetonitrile (molar ratio=1:1) that was a HPLC developing solvent, and then, filtered using a syringe filter and then, the amount of PTX released was identified by HPLC.

Figure 7:
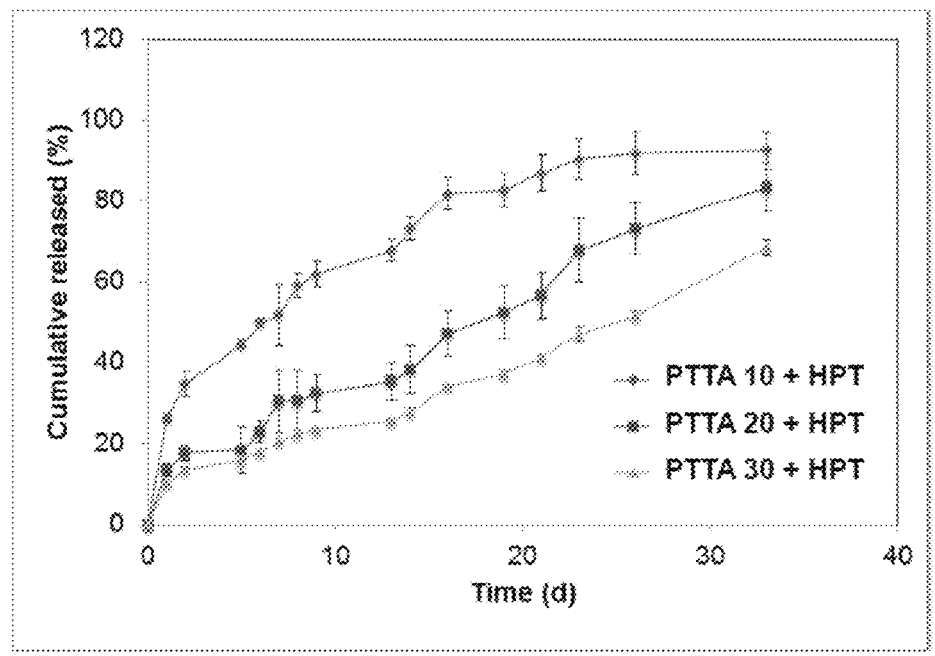
FIG. 7 shows quantitative results of an amount of paclitaxel eluted with respect to PTTA coating number of a drug-eluting stent including PTTD, PTTA, and HPT.

As a result, as shown in FIG. 7, it was confirmed that as PTTA is stacks more, PTX is released slower.

EXAMPLE 10

Evaluation of Cell Proliferation Inhibitory Capacity Performed by Using Stack Structure Including PTTD, PTTA and HPT In the present experiment, smooth muscle cells (SMC) were used, and cultured in a DMEM (containing 10% FBS and 1% penicilin) medium in a standard culture condition (37° C., 5% $CO_2$). SMC were cultured in the density of $5 \times 10^3$ cell/well for 7 days on the stack of PTTD, PTTA and HPT. In detail, a structure (PTX-MTS) used herein included: a stainless steel sample; and a PTTD nanoparticles layer, a 30-layered PTTA nanoparticles layer, and an one-layered HPT nanoparticles layer, which were stacked on the stainless steel sample. In this regard, TCPS was a control in which any sample was not placed on a culture plate. SMC proliferation was analyzed using a cell proliferation reagent WST-1 according to the guide of the manufacturer, and the morphology of the cells was identified using an optical microscope.

Figure 8:
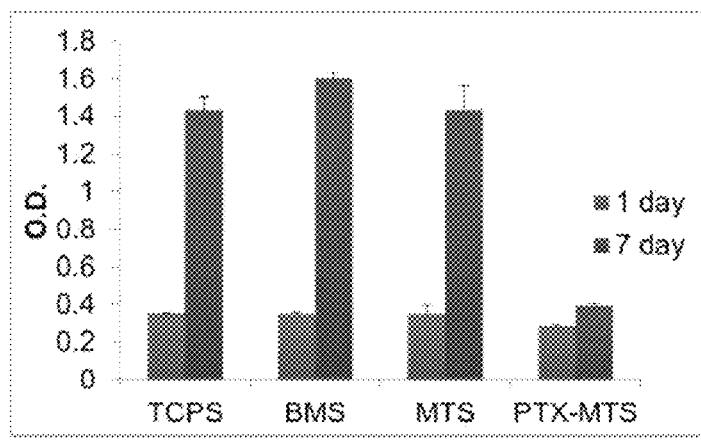
FIG. 8 shows evaluation results of cell proliferation inhibitory ability of a drug-eluting stent including PTTD, PTTA, and HPT.

As shown in FIG. 8, one day after the culture, all groups had similar cell proliferation rates, but 7 days after the culture, on the surface of stainless steel (BMS) and the PTX-free nanoparticles stack surface (MTS), cells proliferation actively occurred, but on the PTX-introduced nanoparticles stack surface (PTX-MTS), cell proliferation hardly occurred.

A drug-eluting stent according to embodiments of the present invention prevents stent restenosis and thrombosis and enables controllable elution of a drug, due to the inclusion of a physiologically active material derivative, such as a heparin derivative to which phenol is introduced, and a plurality of micelle layers to which phenol is introduced. The physiologically active material is stacked to prevent restenosis and thrombosis, which are problems of a conventional drug-eluting stent, and the micelle layers are stacked to enable controllable elution of a drug.

It should be understood that the exemplary embodiments described therein should be considered in a descriptive sense only and not for purposes of limitation, and do not limit the scope of the present invention. Accordingly, the substantial scope of the present invention is defined by the following claims and equivalents thereto.

What is claimed is:

1. A drug eluting stent comprising: a stent body having a surface; and a coating layer having at least three layers disposed over at least a portion of the stent body; wherein the at least three layers of the coating layer comprising:

a first layer disposed over the surface of the stent body, wherein the first layer comprising paclitaxel embedded within at least one layer of crosslinked 4 arm-polypropylene oxide-polyethylene oxide-tyraminedopamine (4 arm-PPO-PEO-TA/DA) conjugates, wherein the crosslinking of the at least one layer of the first layer being formed by reacting the 4 arm-PPO-PEO-TA/DA conjugates with at least one oxidizing agent;

a second layer disposed over the first layer, wherein the second layer comprising paclitaxel embedded within at least one layer of crosslinked 4 arm-polypropylene oxide-polyethylene oxide-tyramine (4 arm-PPO-PEO-TA) conjugates, wherein the crosslinking of the at least one layer of the second layer being formed by reacting the 4 arm-PPO-PEO-TA conjugates with at least one oxidizing agent;

wherein the first layer and the second layer being joined together with crosslinkings formed by reacting at least one oxidizing agent with the tyramine/dopamine attached to the 4 arm-PPO-PEO-TA/DA conjugates of the first layer and the tyramine attached to the 4 arm-PPO-PEO-TA conjugates of the second layer; and a third layer disposed over the second layer, wherein the said third layer comprising a crosslinked heparin-polyethylene glycol-tyramine (heparin-PEG-TA) conjugates, wherein the crosslinking of the third layer being formed by reacting the heparin-PEG-TA conjugates with at least one oxidizing agent;

wherein the second layer and the third layer being joined together with crosslinkings formed by reacting at least one oxidizing agent with the tyramine attached to the 4arm-PPO-PEO-TA conjugates of the second layer and the tyramine attached to the heparin-PEG-TA conjugates of the third layer.

2. The drug eluting stent according to claim 1, wherein the first layer comprising 10, 20, or 30 repeating layers of the crosslinked 4 arm-PPO-PEO-TA/DA conjugates, wherein the repeating layers within the first layer being joined together with crosslinkings formed by reacting at least one oxidizing agent with the tyramine/dopamine attached to the each individual layer of the 4 arm-PPO-PEO-TA/DA conjugates of the first layer.

3. The drug eluting stent according to claim 1, wherein the second layer comprising 10, 20, or 30 repeating layers of the crosslinked 4 arm-PPO-PEO-TA conjugates, wherein the repeating layers within the second layer being joined together with crosslinkings formed by reacting at least one oxidizing agent with the tyramine attached to the each individual layer of the 4 arm-PPO-PEO-TA conjugates of the second layer.

* * * * *